Dec. 11, 1945. F. H. HOWARD Plant Pat. 663
ROSE PLANT
Filed Dec. 26, 1944
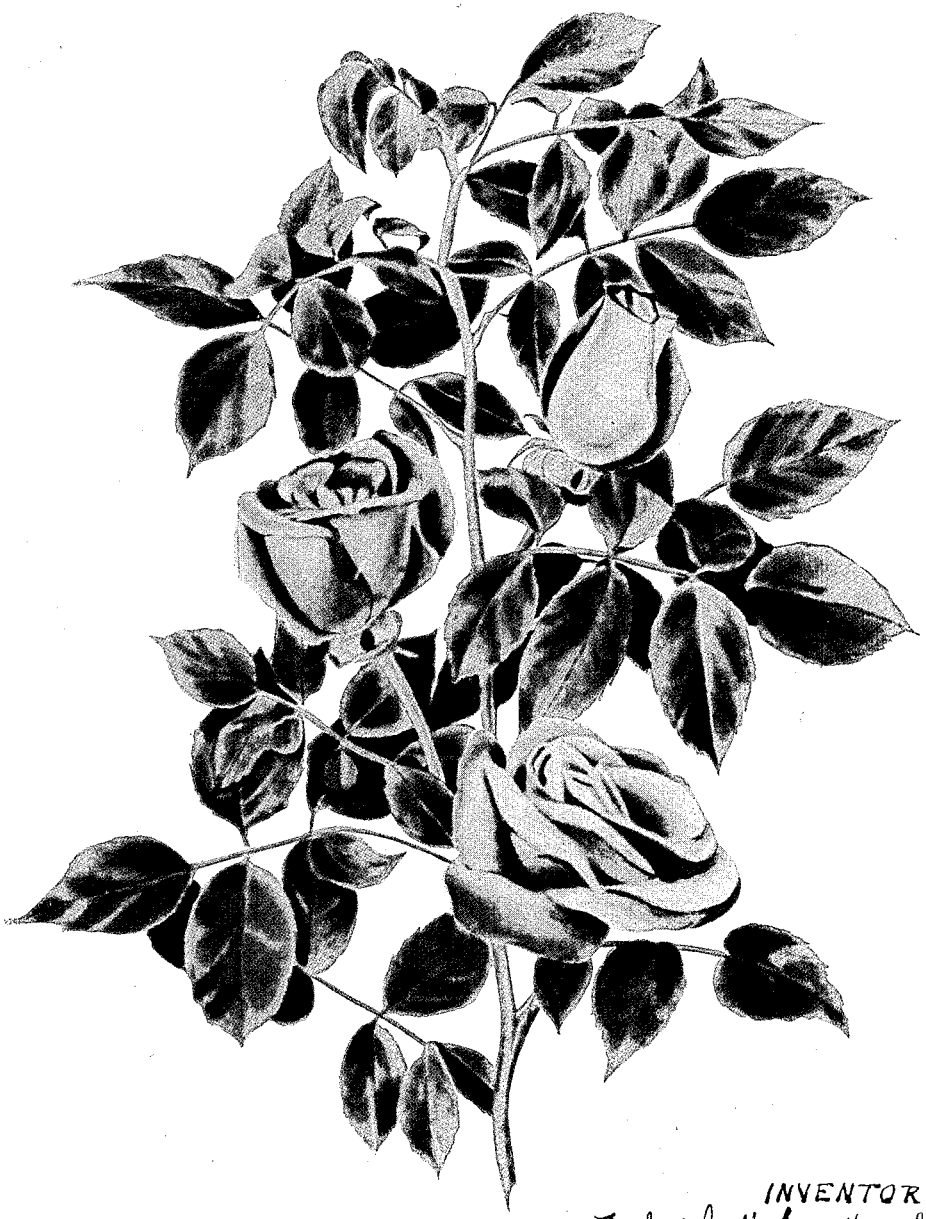
INVENTOR
Frederick Huber Howard
By Orville M. Kile
Plant Pat. Agt.

Patented Dec. 11, 1945

Plant Pat. 663

UNITED STATES PATENT OFFICE

663

ROSE PLANT

Frederick H. Howard, Montebello, Calif., assignor to Howard & Smith, Montebello, Calif.

Application December 26, 1944, Serial No. 569,811

1 Claim. (Cl. 47—61)

My present discovery relates to improvements in hybrid tea roses, specifically of the red everblooming type. The principal improvements lie in the climbing ability of my new variety and the profuse production of very large flowers even on one-year plants.

My new variety originated as a sport of the bush Heart's Desire which is the subject of Plant Patent No. 501. In most respects it is identical with its parent, producing flowers even larger than the parent plant during the cool weather.

Flowers are produced profusely in the field the very first year by my new variety. Nearly all climbing sports of hybrid tea roses send out long vigorous canes the first season but I know of no other climbing sport which produces flowers on the maiden plants. The variety's profuse blooming is even more manifest in the third year.

The illustrations which are a part of this specification show a branch of the new variety with three blooms in various stages of opening. In the original as well as the reproduction, size is greatly reduced.

A detailed description of my new variety follows. Color plate references are to Ridgway's Color Standards and Nomenclature.

*The plant*

Growth: Very vigorous climber, making tremendous growth. Hardy in temperate climates.

Disease resistance: This variety has proved to be exceedingly free from mildew and blackspot.

Blooming habit: Extremely prolific production of large flowers continuously throughout the season. Unlike other known climbing hybrid teas, flowers are profusely produced the first season on plants grown in the field. The profuseness of bloom is even more manifest during the third season.

Stems: Long; strong; short internodes; sharp thorns irregularly spaced.

Foliage: Abundant. Leaves compound with 3 to 7 leaflets.

*Shape.*—Leaflets ovate with acuminate apex.

*Edges.*—Finely serrated.

*Size.*—Small to medium.

*Color.*—Approximately Forest Green (Plate XVII).

*Rachis.*—Grooved above; smooth below.

*Stipules.*—Narrow; medium in length.

Peduncle: Short; sturdy.

*The bloom*

Bud:

*Size.*—Large. Just before unfurling, bud measures 2 to 2½ inches long.

*Shape.*—Long; pointed, with wide base. Inclined to urnshape when half open.

*Color.*—Approximately Carmine (Plate 1) at first. As bud opens it becomes a clear beautiful crimson.

Flower:

*Size.*—Large, averaging approximately 4½ inches in diameter. In cool fall months the flower is a little larger.

*Form.*—Like its parent, the shape of the blooms differs with the seasons. Early in spring the blooms are high-centered, opening finally into cupshape. The hot weather blooms are much more globular in shape, with deep-cupped petals. All petals curl back very slightly at the edges.

*Petalage.*—Double, with 25 to 30 petals. Although the petalage is not great, the flower appears to be heavy because of its form.

Petals:

*Size.*—Outer petals about 2 by 2½ inches.

*Shape.*—Almost circular. Sometimes with slight notch at top. Usually deep-cupped.

*Substance.*—Heavy.

*Color.*—Spring blooms are the same beautiful shade of bright crimson as the buds, without any traces of scarlet or maroon. Ridgway's Color Standards does not show any color like it although it lies between Rose Red (Plate XII) and Carmine (Plate 1), which however is a wide range. Summer blooms lean slightly toward Tyrian Rose (Plate XII).

Longevity: Exceptionally good.

Fragrance: Intense and lasting.

Reproductive organs:

*Pistils.*—Many; closely bunched. *Styles* short and uneven, tinged with red. *Stigmas* light yellow.

*Stamens.*—Many, surrounding bunched pistils. *Filaments* irregular lengths, usually rising above pistils. *Anthers* large and dark yellow.

Having thus disclosed my discovery, I claim:

The new and distinct variety of hybrid tea rose plant substantially as herein shown and described, similar to its parent but characterized particularly by its vigorous climbing habits and the ability to produce continuous and prolific large blooms even on first-year plants.

FRED H. HOWARD.